(12) United States Patent
Jablonski et al.

(10) Patent No.: US 8,513,032 B2
(45) Date of Patent: Aug. 20, 2013

(54) MICROBUBBLES FOR AFFINITY SEPARATION

(75) Inventors: Edward Jablonski, Escondido, CA (US); Thomas Adams, Santa Fe, CA (US)

(73) Assignee: Iris International, Inc., Chatsworth, CA (US)

( * ) Notice: Subject to any disclaimer, the term of this patent is extended or adjusted under 35 U.S.C. 154(b) by 0 days.

(21) Appl. No.: 13/149,551

(22) Filed: May 31, 2011

(65) Prior Publication Data

US 2011/0230644 A1    Sep. 22, 2011

Related U.S. Application Data

(62) Division of application No. 11/718,090, filed as application No. PCT/US2005/040162 on Nov. 3, 2005.

(60) Provisional application No. 60/624,948, filed on Nov. 3, 2004.

(51) Int. Cl.
*G01N 33/544* (2006.01)
*G01N 33/532* (2006.01)

(52) U.S. Cl.
USPC .......................... 436/528; 436/544; 436/523

(58) Field of Classification Search
None
See application file for complete search history.

(56) References Cited

U.S. PATENT DOCUMENTS

| | | | |
|---|---|---|---|
| 4,177,253 A | 12/1979 | Davies et al. | |
| 4,376,110 A | 3/1983 | David et al. | |
| 4,618,525 A | 10/1986 | Chamberlain et al. | |
| 4,824,776 A | 4/1989 | Heller | |
| 4,933,447 A | 6/1990 | Koono et al. | |
| 4,946,778 A | 8/1990 | Ladner et al. | |
| 4,957,656 A * | 9/1990 | Cerny et al. | 424/9.52 |
| 5,116,724 A | 5/1992 | Delaage et al. | |
| 5,270,184 A | 12/1993 | Walker et al. | |
| 5,501,983 A | 3/1996 | Lilja et al. | |
| 5,599,677 A | 2/1997 | Dowell et al. | |
| 5,635,602 A | 6/1997 | Cantor et al. | |
| 5,648,213 A | 7/1997 | Reddy et al. | |
| 5,665,539 A | 9/1997 | Sano et al. | |
| 5,702,896 A | 12/1997 | Collins et al. | |
| 5,749,925 A | 5/1998 | Bocker et al. | |
| 5,759,773 A | 6/1998 | Tyagi et al. | |
| 5,766,849 A | 6/1998 | McDonough et al. | |
| 5,789,165 A | 8/1998 | Oku et al. | |
| 5,849,878 A | 12/1998 | Cantor et al. | |
| 5,888,834 A | 3/1999 | Ishikawa et al. | |
| 5,985,548 A | 11/1999 | Collier et al. | |
| 6,086,540 A | 7/2000 | Bonneville et al. | |
| 6,165,942 A | 12/2000 | Satow et al. | |
| 6,172,208 B1 | 1/2001 | Cook | |
| 6,193,953 B1 | 2/2001 | Lohrmann et al. | |
| 6,214,566 B1 | 4/2001 | Asa et al. | |
| 6,245,318 B1 | 6/2001 | Klibanov et al. | |
| 6,511,809 B2 | 1/2003 | Baez et al. | |
| 6,531,278 B1 | 3/2003 | Weimer et al. | |
| 6,531,288 B1 | 3/2003 | Snutch | |
| 6,723,303 B1 | 4/2004 | Quay | |
| 7,649,001 B2 | 1/2010 | Shiraishi et al. | |
| 2002/0064779 A1 | 5/2002 | Landegren et al. | |
| 2003/0104359 A1 | 6/2003 | Cuthbertson et al. | |
| 2003/0138432 A1 | 7/2003 | Glazier | |
| 2004/0142323 A1 | 7/2004 | Caine Boyde | |
| 2005/0026161 A1 | 2/2005 | Jablonski | |
| 2005/0170398 A1 | 8/2005 | Van Berkel et al. | |
| 2008/0131883 A1 | 6/2008 | Adams et al. | |
| 2009/0176207 A1 | 7/2009 | Neuman | |
| 2009/0246781 A1 | 10/2009 | Klem et al. | |

FOREIGN PATENT DOCUMENTS

| | | |
|---|---|---|
| EP | 0359246 A2 | 3/1990 |
| EP | 0359246 A3 | 3/1990 |
| EP | 0488152 | 6/1992 |
| EP | 1249500 A | 10/2002 |
| GB | 2091729 | 8/1982 |
| WO | WO 92/16841 | 10/1992 |
| WO | WO 93/07883 | 4/1993 |
| WO | WO 96/15130 | 5/1996 |
| WO | WO 97/00446 A1 | 1/1997 |
| WO | WO 97/40049 | 10/1997 |
| WO | WO 98/53857 | 12/1998 |
| WO | WO 00/41524 | 7/2000 |
| WO | WO 01/96608 | 12/2001 |
| WO | WO 02/068695 | 9/2002 |
| WO | WO 02/083951 | 10/2002 |
| WO | WO 03/011824 | 2/2003 |
| WO | WO 03/076943 | 9/2003 |
| WO | WO 2004/042030 | 5/2004 |
| WO | WO 2006/034441 | 3/2006 |
| WO | WO 2006/137932 | 12/2006 |
| WO | WO 2006/137933 | 12/2006 |
| WO | WO 2009/105264 | 8/2009 |

OTHER PUBLICATIONS

In re Australian Patent Application No. 2005333156, Examiner's First Report, Dated May 4, 2010.
In re Australian Patent Application No. 2005333157, Examiner's First Report, Dated Jun. 2, 2010.
In re Chinese Patent Application No. 200580038082.8, Examiner's First Report, Dated Dec. 11, 2009.
In re European Patent Application No. 03 810 829.6-1223, Communication Pursuant to Article 94(3) EPC, Dated Mar. 4, 2008.
In re European Patent Application No. 03 810 829.6-1223, Supplementary European Search Report, Dated Nov. 20, 2006.
In re European Patent Application 05858304.8, Communication According to Article 94(3) EPC, Dated Nov. 10, 2008.
In re European Patent Application 05858303.0, Supplementary Search Report, Dated Jun. 26, 2009.

(Continued)

*Primary Examiner* — Shafiqul Haq
(74) *Attorney, Agent, or Firm* — Duane Morris LLP

(57) ABSTRACT

The present invention relates to methods, compositions and kits for affinity isolation, affinity purification and affinity assay based on microbubbles coated with an affinity molecule. Particularly, the invention provides protein microbubbles coated with an affinity molecule. In addition, the invention provides glass microbubbles coated with an affinity molecule. Methods of using the microbubbles of the invention for isolating analytes and cells are specifically provided.

11 Claims, No Drawings

(56) References Cited

OTHER PUBLICATIONS

In re European Patent Application 05858303.0, European Search Report, Dated Jul. 8, 2009.
In re European Patent Application 05858304.8, Communication According to Article 94(3) EPC, Dated Sep. 4, 2009.
In re European Patent Application No. 03 810 829.6-1223, Communication Pursuant to Article 94(3) EPC, Dated Sep. 28, 2009.
In re European Patent Application 05858303.0, Communication According to Article 94(3) EPC, Dated Oct. 2, 2009.
In re European Patent Application 05858304.8, Annex to Communication Dated Apr. 14, 2010.
In re European Patent Application 05858304.8, Annex to Communication Dated Jun. 1, 2010.
In re European Patent Application No. 03 810 829.6-1223, Communication Pursuant to Article 94(3) EPC, Dated Aug. 31, 2010.
In re European Patent Application 09713301.1-1223, Communication pursuant to Article 94(3), Dated Jan. 18, 2011.
European Search Report form counterpart European Patent Application No. 10190637.8, Dated Feb. 21, 2011.
Extended Search Report from counterpart European Patent Application No. 10190637.8, Date Feb. 28, 2011.
Supplemental Search Report from counterpart EP Application No. 03810829.6, Nov. 20, 2006.
Supplemental Search Report from counterpart EP 05858304 dated Aug. 8, 2008.
Supplemental Search Report from counterpart EP 05858304 dated Aug. 12, 2008.
PCT International Search Report for foreign counterpart International Application No. PCT/US03/35153, Aug. 31, 2004.
PCT International Preliminary Report from counterpart International Application No. PCT/US03/35153, Sep. 18, 2007.
International Search Report from counterpart International Application No. PCT/US05/040162, Dated Feb. 16, 2007.
International Report on Patentability from counterpart International Application No. PCT/US05/040162, Dated May 8, 2007.
International Search Report for foreign counterpart International Application No. PCT/US2009/001114 Dated Jun. 22, 2009.
Written Opinion for foreign counterpart International Application No. PCT/US2009/001114 Dated Jun. 22, 2009.
Non Final Office Action, U.S. Appl. No. 10/701,347, Mail Date Sep. 22, 2006.
Non Final Office Action, U.S. Appl. No. 10/701,347, Mail Date Jul. 24, 2007.
Final Office Action, U.S. Appl. No. 10/701,347, Mail Date Mar. 17, 2008.
Non Final Office Action, U.S. Appl. No. 11/718,379, Mail Date Aug. 5, 2010.
Non Final Office Action, U.S. Appl. No. 10/701,347, Mail date Nov. 23, 2010.
Non Final Office Action, U.S. Appl. No. 11/718,379, Mail Date Feb. 1, 2011.
Non Final Office Action, U.S. Appl. No. 11/718,090, Mail Date Mar. 1, 2011.
Non Final Office Action, U.S. Appl. No. 11/718,090, Mail Date May 20, 2011.
Barletta, et al. "immuno-polymerase chain reaction as a unique molecular tool for detection of infectious agents"; Expert Opinion Med. Diagn. 1:(2); pp. 267-288; (2007).
Bazemore, et al, "Kinetic analysis of pairing and strand exchange catalyzed by RecA.", J Biol. Chem. 272(23); pp. 14672-14682 (1997).
Bird, Robert, et al; "Single-Chain Antigen-Binding Proteins"; Science, vol. 242; pp. 423-426; Oct. 1998.
Boyle et al. "Cancer incidence and mortality in Europe, 2004"; Annals of Oncology 16; pp. 481-488; (2005).
Cote et al., "Generation of human monoclonal antibodies reactive with cellular antigens"; Proc. Natl. Acad. Sci. USA, 80; pp. 2026-2030; (1983).

DeLisi C, . "Detection and analysis of recognition and selection in the immune response.", Bulletin of Mathematical Biology 39: pp. 705-719 (1977).
Diamandis, et al. "Detection of Prostate Cancer Relapse With Prostate Specific Antigen Monitoring at Levels of 0.001 to 0.1 ug/L"; Journal of Urology 157(3): pp. 913-918; (Mar. 1997).
Doherty et al. "Undetectable ultrasensitive PSA after radical prostatectomy for prostate cancer predicts relapse-free survival"; Br. J. Cancer 83(11): XP-002522512; pp. 1432-1436 (2000).
Ellis et al.; "Early Detection of Recurrent Prostate Cancer with an Ultrasensitive Chemilunescent Prostate-Specific Antigen Assay"; Adult Urology 50(4):pp. 573-579 (1997).
Furuya et al.; "An immuno-polymerase chain reaction assay for human interleukin-18"; J. Immunol. Methods; pp. 238:173-180, (2000).
Hendrickson et al.; "High sensitivity multianalyte immunoassay using covalent DNA-labeled antibodies and polymerase chain reaction"; Nucleic Acids Research vol. 23 No. 3; pp. 522-529; (1995).
Hermanson; "Nucleic Acid and Oligonucleotide Modification and Conjugation" Bioconjugate Techniques, pp. 639-666, (1996).
Hirn-Scavennec, et al., "Elimination of Lukemia Cells from Human Bone Marrow Using Floating Beads"; Transplantation 46(4) pp. 558-563 (Oct. 1988).
Holmberg, et al.; Surfactant—Protein Mixtures Ch. 14; Surfactant and Polymers in Solutions; pp. 305-315; (2002).
Hombach et al.; "A novel 34-kd protein co-isolated with the IgM molecule in surface IgM-expressing cells"; EMBO 7(11) XP009027621; pp. 3451-3456 (1988).
Huse et al; "Generation of a Large Combinatorial Library of the Immunoglobulin Repertoire in Phage Lambda"; . Science, 246; pp. 1275-1281; (Dec. 8, 1989).
Huston et al.; "Protein engineering of antibody binding sites: Recovery of specific activity in an anti-digoxin single-chain Fv analogue produced in *Escherichia coli*"; Proc. Natl. Acad. Sci. USA, 85; pp. 5879-5883 (Mar. 9, 1988).
Jablonski, Ed, et al.; "Ther merging of nucleic acid detection and immunoassays"; Moleculoar Diagnostics; (IVDT) ; 4 pages; Nov./Dec. 2006.
Jablonski et al.; "Preparation of oligodeoxynucleotide-alkaline phosphatase conjugates and their use as hybridization probes"; Nucleic. Acids Research vol. 14 No. 15; pp. 6115-6128 (1986).
Jablonski, et al.; "Detecting Prostate-Specific Antigen (PSA) Using Nucleic Acid Detection Immunoassay (NADIA) Technology"; Clinical Chemistry 53(6S): pp. A107-A109 (Jul. 15, 2007).
Jeanene Swanson; "The Rise of ImmunoPCR"; GenomeWeb, Aug. 30, 2007; pp. 1-4.
Joerger et al.; "Analyte Detection with DNA-Labeled Antibodies and Polymerase Chhain Reaction"; Clin. Chem. 41/9; pp. 1371-1377; (1995).
Junker et al.; "The Biologic Lower Detection Limit of Six Ultrasensitive PSA Assays"; Anticancer Research 19; :pp. 2625-2658 (1999).
Kilbanov, Alexander; "Targeted delivery of gas-filled microspheres, contrast agents for ultrasound imagining"; Advance Drug Delivery Reviews, vol. 37; pp. 139-157; (1999).
Klee et al., "Development of a Highly Sensitive Immunochemiluminometric Assay for Prostate-Specific Antigen"; Adult Urology 44(1): 76-82 (Jul. 1994).
Kohler and Milstein, "Continuous cultures of fused cells secreting antibody of predefined specificity"; Nature, vol. 256: pp. 495-497 (1975).
Lindner et al., "Molecular imaging with contrast ultrasound and targeted microbubbles "; Journal of Nuclear Cardiology 11(2):215-221, especially Figure 1 (2004).
McKie et al., J. "Development of a quantitative immuno-PCR assay and its use to detect mumps-specific IgG in serum"; Journal of Immunol. Methods 261; pp. 167-175 (2002).
Manetti et al. J. "Prostate-specific antigen is increased in female patients with Cushing's disease "; J Endocrinol. Invest. vol. 25; pp. RC29-RC31 (2002).
Molecular Probes; "Anti-Fluorescein Antibodies Product Information" (Feb. 2001).
Molecular Probes; "Anti-Tetramethylrhodamine Antibodies Product Information" (Feb. 2001).

Morrison, et al.; Chimeric human antibody molecules: Mouse antigen-binding domains with human constant region domains; Proc. Natl. Acad. Scie., 81; pp. 6851-6855 (1984).
Morrissey et al.; "Nucleic Acid Hybridization Assays Employing dA-Tailed Capture Probes"; Anal Biochem 181; pp. 345-359 (1989).
Moul; "Prostate Specific Antigen Only Progression of Prostate Cancer"; J. Urology 163; pp. 1632-1642 (2000).
Niemeyer, et al, "Oligonucleotide-directed self-assembly of proteins: semisynthetic DNA-streptavidin hybrid molecules as connectors for the generation of macroscopic arrays and the construction of supramolecular bioconjugates."; Nucleic Acid Research 22(25); pp. 5530-5539 (1994).
Nilsson et al.; "A systematic overview of radiation therapy effects in prostate cancer"; Acta Oncologica 434); pp. 316-381 (2004).
Otzen, et al.; "Protein Unfolding in Detergents: Effect of Micelle Structure, Ionic Strength, pH, and Temperature"; Biophysical Journal 83; pp. 2219-2230, Oct. 2002.
Prott, et al.; "Biochemical Relapse of Prostate Cancer. Evidence after Radical Surgery"; AntiCancer Research 23; pp. 979-982 (2003).
Sano et al.; "Immuno-PCR: Very Sensitive Antigen Detection by Means of Specific Antibody-DNA Conjugates"; Science vol. 258; pp. 120-122; Oct. 2, 1999.
Saito, et al.; "Detection of Human Serum Tumor Necrosis Factor-a in Healthy Donors, using a Highly Sensitive Immuno-PCR Assay"; Clinical. Chemistry. 45:5; pp. 665-669 (1999).
Schick et al.; The TAPA-1 Molecule is Associated on the Surface of B Cells with HLA-DR Molecules[1]; Journal of Immunology 151(8); pp. 4090-4097 (Oct. 15, 1993).
Seto, et al.; Development of ultra-high sensitivity bioluminescent enzyme immunoassay for prostate-specific antigen (PS) using firefly luciferase; Luminescence 16; XP-002522510; pp. 285-290 (2001).
Stamey, Thomas; "Lower limits of detection, biological detection limits, functional sensitivity, or residual cancer detection limit? Sensitivity reports on prostate-specific antigen assays mislead clinicians"; Clin. Chem. 42(6); pp. 849-852 (1996).
Sugawara et al.; A highly sensitive immuno-polymerase chain reaction assay for human angiotensinogen using the identical first and second polyclonal antibodies; Clinica Chemica. Acta 299; pp. 45-54; (2000).
Takeda et al.; Construction of chimaeric processed immunoglobulin genes containing mouse variable and human constant region sequences; Nature vol. 314; pp. 452-454 (1985).
Taylor et al; "The relationship of ultrasensitive measurements of prostate-specific antigen levels to prostate cancer recurrence after radical prostatectomy"; Journal Compilation vol. 98; XP-002522514; pp. 540-543 (2006).
Tsutsui et al.; "The use of microbubbles to target drug delivery"; Cardiovascular Ultrasound 2(23); pp. 1-7, especially pp. 1-2 (2004).
Tyagi and Kramer,; "Molecular Beacons: Probes that Fluoresce upon Hybridization"; Nt. Bitechnol 14; pp. 303-308; (1996).
Tyagi et al.; "Wavelength-shifting molecule beacons"; Nature Biotechnology vol. 18; pp. 1191-1196; Nov. 18, 2000.
UK Prostate Cancer incidence statistics, http://info.cancer-researchuk.org/cancerstats/types/prostate/incidence/ (last accessed Feb. 27, 2009).
Vassilikos et al.; "Relapse and Cure Rates of Prostate Cancer Patients After Radical Prostatectomy and 5 Years of Follow-up"; Clinical Biochemistry vol. 33 No. 2; XP-002522511; pp. 115-123 (Mar. 2000).
Vaisanen et al.; "Characterization and processing of prostate specific antigen (hK3) and human glandular kallikrein (hK2) secreted by LNCaP cells"; Prostate Cancer and Prostatic Disease 2; pp. 91-97 (1999).

Walker, Nigel J.; "A Technique Whose Time Has Come"; Science vol. 296; pp. 557-558 (2002).
Ward et al.; "Binding activities of a repertoire of single immunoblobulin variable domains secreted from *Escherichia coli*"; Nature, vol. 334; pp. 544-546 (1989).
Weller et al.; "Ultrasound Contrast Microbubbles Targeted to Tumor Angiogenesis Specifically Bind Tumor-Derived Endothelial Cells"; Proceedings of $2^{nd}$ hoint EMBS/BMES Conference, Houston, TX, Oct. 23-26, 2002, especially p. 897.
William Check, PhD, "PCR and ELISA adaptations—will they fly?"; College of American Pathologist Journal; Jul. 2007; 6 pages.
Witherspoon et al. "Sensitive Prostate Specific Antigen Measurements Identify Men With Long Disease-Free Intervals and Differentiate Aggressive From Indolent Cancer Recurrences Within 2 Years After Radical Prostatectomy", The Journal of Urology 157:1322-1328 Apr. 1997.
In re Chinese Patent Application No. 200580038082.8, Examiner's Second Report, Dated Aug. 24, 2011.
Extended Search Report from counterpart European Patent Application No. 10184768.9, Date Apr. 27, 2011.
Non Final Office Action, U.S. Appl. No. 11/718,379, Mail Date Jul. 21, 2011.
Non Final Office Action, U.S. Appl. No. 12/378,965, Mail Date Sep. 28, 2011.
Lind et ai, J Immunological Mehtods 304:107-116,2005.
Means G E et al: "Chemical Modifications 6 of Proteins: History and Applications", Bioconjugate Chemistry, ACS, Washington, DC, US, vol. 1, No. 1, Jan. 1, 1990, pp. 2-12, Xp000236570.
Patel et al (Adult Urology, 65:942-946, 2005.
Partial European Search Report form counterpart European Patent Application No. 10184768.9 dated Jan. 28, 2011.
International Search Report from counterpart International Application No. PCT/US2005/040133 dated Sep. 20, 2007.
International Preliminary Report on Patentability from counterpart International Application No. PCT/US2005/040133 dated Aug. 21, 2007.
Cookson et al.; "Variation in the Definition of Biochemical Recurrence in Patients Treated for Localized Prostate Cancer: The American Urological Association Prostate Guidelines for Localized Prostate Cancer Update Panel Report and Recommendations for a Standard in the Reporting of Surgical Outcomes" J. Urology 177(2); pp. 540-545, (Feb. 2007).
McCarthy, D.; "Cell Preparation"; Flow Cytometry: Principles and Applications, Edited by M.G. Macey Chapter 2.
Niemeyer et al.; "DNA-Directed Immobilization: Efficient, Reversible, and Site-Selective Surface Binding of Proteins by Means of Covalent DNA Streptavidin Conjugates"; Analytical Biochemistry, Academic Press, vol. 268, No. 1; pp. 54-63 (Mar. 1, 1999), XP-002176566.
Richard J. Simpson: "Proteins and Proteomics: A Laboratory Manual", 2003, Cold Spring Harbor Laboratory Press, XP008109069, Ramsby et al, Chapter 3: Preparation of Cellular and Subcellular Extracts *Ramsby et al.; "Preparation of Cellular and Subcellular Extracts"; Ch. 3; p. 91-109.
Trock et al..; "Prostate cancer-specific survival in men with biochemical recurrence after prostatectomy: Impact of salvage radiotherapy vs. observation"; ASCO Urogenitary Cancers Symposium, Abstract No. 85 http://www.asco.org/ASCOv2/Meetings/Abstracts?&vmview=abst_detail_view&confID=54&abstractID=20509 (Feb. 2008).
McCarthy, D.; "Cell Preparation"; Flow Cytometry: Principles and Applications, Edited by M.G. Macey Chapter 2, 2007.

* cited by examiner

MICROBUBBLES FOR AFFINITY SEPARATION

RELATED APPLICATIONS

This application is a Divisional of U.S. application Ser. No. 11/718,090, filed on Mar. 13, 2009, which claims priority from National Stage Application No. PCT/US05/40162, filed on Nov. 3, 2005, which claims priority to Provisional Application No. 60/624,948, filed on Nov. 3, 2004, the entire disclosures of which are hereby incorporated by reference in their entirety.

FIELD OF THE INVENTION

This invention relates to methods, compositions and kits for affinity isolation, affinity purification, and affinity assay based on microbubbles coated with an affinity molecule.

BACKGROUND OF INVENTION

The field of isolating cells, virus, bacteria and soluble molecules has used various types of particles as a solid phase to absorb or bind to the target of interest. For example, magnetic particles, when coated with a ligand, such as an antibody, can bind to a target cell or soluble protein. The bound target on the magnetic particle effects a separation of the target from other cells types or proteins. There have been various improvements on this original work and commercial examples have been available for years.

Others have used latex particles, liposomes, milk fat globules, plastic particles such as polystyrene and polyethylene and polypropylene, nylon etc. As capture supports, each of these has its own particular attributes and problems. Non-specific binding of non-target cells and proteins is the most common problem encountered in these methods, resulting in imperfect separation. Additionally, most methods require at least one additional step following binding to effect separation of unbound species from the particle-bound, e.g. for magnetic particles a magnetic field must be applied, centrifugation is sometimes used to separate the particles from solution or filtration of the particles from solution.

In general, the time required to bind the target cells or proteins is related to the surface area of the particles and the quantity of particles per unit volume of solution. The smaller the particle the more rapid the binding due to increased surface area Unfortunately, greater surface area generally increases non-specific binding.

Separation methods may, depending on the nature or principle of the separation, co-isolate different particles. This is apparent in separations based on gravity centrifugation in which particles and cells or other species may co-pellet. In addition some cell types such as macrophages and monocytes may themselves non-specifically ingest the particles and can be isolated along with the target cells. While individual limitations of the previous technology may be minimized or avoided by taking certain steps or precautions, certain limitations are inherent and cannot be entirely overcome. The fact that there are many different approaches with varying degrees of success suggests that a better solution to the problem is needed.

The optimal separation agent would have an infinite surface area with zero non-specific interaction so that the binding would occur instantaneously and minimize binding to non-target cells or soluble molecules. Ideally, the agent should separate itself from the cell suspension or soluble molecule solution without entrapping non-target cells or molecules respectively.

SUMMARY OF THE INVENTION

The present invention provides compositions for use in affinity isolation or affinity assay comprising microbubbles that are covalently coated with an affinity molecule. In one embodiment of the invention, the microbubbles are protein microbubbles, such as albumin microbubbles. The protein microbubbles may be formed by the introduction of a gas into a solution of protein, for example, by sonication. In one aspect of the invention, gas may be introduced into the protein through a process comprising heating a solution of protein. In another embodiment, the protein microbubbles may be stabilized, for example, by denaturing the protein or treatment with $Cr^{+++}$.

In another embodiment of the invention, the microbubbles are glass microbubbles. In one aspect of the invention, the glass microbubbles have a density of about 0.6 g/cc and an average diameter of about 30 μm.

According to the invention, the affinity molecule can be a receptor, a ligand, or an antibody. Alternatively, the affinity molecule can be biotin, avidin or streptavidin.

The affinity molecule may be directly coupled to the microbubble, for example, by using a heterobifunctional reagent such as sulfosuccinimidyl 4-(N-maleimidomethyl) cyclohexane-1-carboxylate. In another embodiment of the invention, the affinity molecule is indirectly coupled to the microbubble, such as through the interaction of at least one other molecule. In one aspect of the invention, the microbubble is directly coupled to streptavidin and the affinity molecule is biotinylated, such that the streptavidin and biotin interact to couple the affinity molecule to the microbubble.

According to one embodiment of the invention, the affinity molecule may be directly coupled to the microbubble through an epoxy coating on the microbubble. In another embodiment, the affinity molecule is coupled through an amine functional group on the microbubble.

In one aspect of the invention, glass microbubbles are treated to generate reactive surface residues, which are in turn reacted with 3-aminopropyltriethoxy silane, generate amines. In another aspect, glass microbubbles are cis-diol coated and the affinity molecule is directly coupled to the glass through the cis-diol coating. The cis-diol coating can be generated, for example, by treating the glass microbubbles to generate reactive surface hydroxyl residues, reacting the hydroxyl residues with 3-glycidoxypropyltrimethoxysilane to generate epoxy functional residues, and treating the epoxy functional residues with acid to convert the epoxy function to cis-diol functions.

The present invention also provides a method for generating protein microbubbles for use in affinity isolation or affinity assay. In one aspect, the method comprises heating a solution of protein. In another aspect of the method, a solution of protein is treated ultrasonically to introduce gas into the solution, thereby generating protein microbubbles. In yet another aspect of the method, the solution of protein is treated mechanically in the presence of a gas or a gas mixture.

In alternative aspects of the invention, the gas is air and the protein is albumin. The protein microbubbles may be stabilized, for example by treatment with $Cr^{+++}$.

The present invention also provides a method for generating microbubbles for use in affinity isolation or affinity assay comprising providing microbubbles; and coating the microbubbles with an affinity molecule.

In another embodiment of the invention, methods for affinity isolation or affinity assay of a species are provided. According to these embodiments, the method comprises the steps of providing microbubbles coated with an affinity molecule in a solution, contacting the microbubbles with a species that interacts with the affinity molecule in a solution, thereby generating microbubbles coated with the species, and allowing the microbubbles coated with the species to float to the top of the solution, thereby separating the species from the solution.

In one aspect of this embodiment, the species is a receptor, a ligand, or an antigen. In one embodiment, the species is an analyte. In alternative embodiments, the species is a virus or a cell.

In another aspect of the invention, protein microbubbles, particularly albumin microbubbles can be treated with detergent, pressure or vacuum to release the species.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise. As used herein, "or" means "and/or" unless stated otherwise. Furthermore, use of the term "including" as well as other forms, such as "includes," and "included," is not limiting. As used herein, "can" means "may" unless stated otherwise.

The section headings used herein are for organizational purposes only and are not to be construed as limiting the subject matter described. All documents, or portions of documents, cited in the application including, but not limited to, patents, patent applications, articles, books, manuals, and treatises are hereby expressly incorporated by reference in their entirety for any purpose.

Definitions

Before proceeding further with a description of the specific embodiments of the present invention, a number of terms will be defined and described in detail.

Unless specific definitions are provided, the nomenclatures utilized in connection with, and the laboratory procedures, techniques and methods described herein are those known in the art to which they pertain. Standard chemical symbols and abbreviations are used interchangeably with the full names represented by such symbols. Thus, for example, the terms "carbon" and "C" are understood to have identical meaning. Standard techniques may be used for chemical syntheses, chemical modifications, chemical analyses, pharmaceutical preparation, formulation, delivery, and treatment of patients. Standard techniques may be used for recombinant DNA methodology, oligonucleotide synthesis, tissue culture and the like. Reactions and purification techniques may be performed e.g., using kits according to manufacturer's specifications, as commonly accomplished in the art or as described herein. The foregoing techniques and procedures may be generally performed according to conventional methods well known in the art and as described in various general or more specific references that are cited and discussed throughout the present specification. See e.g., Sambrook et at. Molecular Cloning: A Laboratory Manual (2d ed., Cold Spring Harbor Laboratory Press, Cold Spring Harbor, N.Y. (1989)), Harlow & Lane, Antibodies: A Laboratory Manual (Cold Spring Harbor Laboratory Press, Cold Spring Harbor, N.Y. (1988)), which are incorporated herein by reference in their entirety for any purpose.

"Bubble," as used herein refers to a small, hollow and lightweight globule, typically a small spherical volume of gas encased within a thin film. Bubbles can be filled with any gas, including, but not limited to oxygen, nitrogen, carbon dioxide, helium, fluorocarbon gases and various combinations thereof, such as air. The thin film may be any material that can encase a small volume of gas, such as an insoluble protein or lipid; a polymeric or non polymeric material; a solid such as a metal; a solid glass, ceramic or similar material; or a plastic, such as polystyrene, polyethylene, polypropylene, nylon, etc. In a preferred embodiment, the thin film is albumin. In another preferred embodiment, the thin film is borosilicate glass. In one embodiment, the thin film is stable under the conditions and solutions it is exposed to. In another embodiment, the bubble can be selectively burst, crushed or solubilized. "Microbubbles" are small bubbles, generally in the range of 0.1 to 100 microns, typically 1 to 50, and frequently 2 to 20 or 2 to 30 microns in diameter.

The term "analyte," as used herein, refers to any substance that it is desirable to detect in an assay, and which may be present in a sample. The analyte can be, without limitation, any substance. In a preferred embodiment of the invention, an analyte comprises a substance for which there exists a naturally occurring antibody or for which an antibody can be prepared. The analyte may, for example, be a protein, a polypeptide, a hapten, a carbohydrate, a lipid, a drug, a cell, a cellular subcomponent or organelle (e.g., lysozomes, mitochondria) or any other of a wide variety of biological or non-biological molecules, complexes or combinations thereof. In another embodiment, the analyte is an antibody. In still another embodiment, the analyte is a nucleic acid (DNA, RNA, PNA and nucleic acids that are mixtures thereof or that include nucleotide derivatives or analogs)

Polyvalent ligand analytes that can be detected using compositions, methods and kits of the present invention will normally be poly(amino acids), i.e., polypeptides and proteins, polysaccharides, nucleic acids, and combinations thereof. Such combinations include components of cells, tissues, bacteria, viruses, cell walls, cell membranes, cellular organelles, chromosomes, genes, mitochondria, nuclei and the like. According to one aspect of the invention, certain analytes do not contain nucleic acid.

A wide variety of protein analytes may be advantageously detected using the methods of the present invention. Such protein analytes can be classified according to family, with each family having similar structural features, biological functions, relationship to specific microorganisms (particularly disease causing microorganisms), and the like. Protein families of particular interest for the present invention include, for example, immunoglobulins, cytokines, enzymes, hormones, cancer antigens, nutritional markers, tissue specific antigens, and biowarfare agents. These protein analytes may be present in blood, serum, plasma, spinal fluid, synovial fluid, saliva, urine, semen, prosthetic fluid, cells or tissues.

The following are examples of classes of protein analytes related by structure that may be detected using the compositions, methods and kits of the present invention:

protamines
histones
albumins
globulins
scleroproteins
phosphoproteins
mucoproteins The following examples are clinically important proteins found in human plasma that may be detected using the compositions, methods and kits of the present invention:
$\alpha_1$-Lipoprotein
$\alpha 1$-Antitrypsin
Transcortin
4.6S-Postalbumin
Tryptophan-poor
$\alpha_1$-Glycoprotein
$\alpha_{1X}$-Glycoprotein
Thyroxin-binding globulin
Inter-$\alpha$-trypsin-inhibitor
Gc-globulin
   (Gc 1-1)
   (Gc 2-1)
   (Gc 2-2)
Haptoglobin
   (Hp 1-1)
   (Hp 2-1)
   (Hp 2-2)
Ceruloplasmin
Cholinesterase
$\alpha_2$-Lipoprotein(s)
Myoglobin
C-Reactive Protein
$\alpha_2$-Macroglobulin
$\alpha_2$-HS-glycoprotein
Zn-$\alpha_2$-glycoprotein
$\alpha_2$-Neuramino-glycoprotein
Erythropoietin
$\beta$-lipoprotein
Transferrin
Hemopexin
Fibrinogen
Plasminogen
$\beta_2$-glycoprotein I
$\beta_2$-glycoprotein II
Immunoglobulin G
(IgG) or $\gamma$G-globulin
   Mol. formula: $\gamma 2 k 2$ or $\gamma 2 \lambda 2$
Immunoglobulin A (IgA) or $\gamma$A-globulin
   Mol. formula: $(\alpha_2 \kappa_2)^n$ or $(\alpha_2 \kappa_2)^n$
Immunoglobulin M (IgM) or $\gamma$M-globulin
   Mol. formula: $(\mu_2 \kappa_2)^5$ or $(\mu_2 \lambda_2)_5$
Immunoglobulin D (IgD) or $\gamma$D-Globulin ($\gamma$D)
   Mol. formula: $(.delta._2 \kappa_2)$ or $.delta._2 \kappa_2)$
Immunoglobulin E (IgE) or $\gamma$E-Globulin ($\gamma$E)
   Mol. formula: $(\epsilon_2 \kappa_2)$ or $(\epsilon_2 \lambda_2)$
Free $\kappa$ and $\lambda$ light chains
Complement factors:
  C'1
  C'1q
  C'1r
  C'1s
  C'2
  C'3
  C'3
  $\beta_1$ A
  $\alpha_2$ D
  C'4
  C'5
  C'6
  C'7
  C'8
  C'9

Important blood clotting factors that may be detected using the compositions, methods and kits of the present invention include the examples listed in the Table below.

TABLE 1

BLOOD CLOTTING FACTORS

| International Designation | Name |
|---|---|
| I | Fibrinogen |
| II | Prothrombin |
| IIa | Thrombin |
| III | Tissue thromboplastin |
| V and VI | Proaccelerin, accelerator globulin |
| VII | Proconvertin |
| VIII | Antihemophilic globulin (AHG) |
| IX | Christmas factor plasma thromboplastin component (PTC) |
| X | Stuart-Prower factor, autoprothrombin III |
| XI | Plasma thromboplastin |
| XIII | Fibrin-stabilizing factor |

Important protein hormones that may be detected using the compositions, methods and kits of the present invention include:
  Peptide and Protein Hormones
  Parathyroid hormone (parathromone)
  Thyrocalcitonin
  Insulin
  Glucagon
  Relaxin
  Erythropoietin
  Melanotropin (melanocyte-stimulating hormone; intermedin)
  Somatotropin (growth hormone)
  Corticotropin (adrenocorticotropic hormone)
  Thyrotropin
  Follicle-stimulating hormone
  Luteinizing hormone (interstitial cell-stimulating hormone)
  Luteomammotropic hormone (luteotropin, prolactin
  Gonadotropin (chorionic gonadotropin)
  Tissue Hormones
  Secretin
  Gastrin
  Angiotensin I and II
  Bradykinin
  Human placental lactogen
  Cytokines
  IL 1
  IL 2
  IL 4
  IL 6
  Il 8
  Il 10
  EGF
  TNF
  NGF
  Cancer Antigens
  PSA
  CEA
  $\alpha$-fetoprotein
  Acid phosphatase
  CA19.9
  CA125
  Tissue Specific Antigens
  alkaline phosphatase
  myoglobin
  CPK-MB Troponin
BNP
Pro-BNP
Calcitonin
Myelin basic protein
Peptide Hormones from the Neurohypophysis
Oxytocin
Vasopressin
Releasing factors (RF) CRF, LRF, TRF, Somatotropin-RF, GRF, FSH-RF, PIF, MIF
Ricin
Diptheria toxin
Botulism toxin
*Staphylococcus enterotoxin* B Bacteria and viruses are also analytes that may be detected using the compositions, methods and kits of the present invention. Included among these biological analytes are, among others:

Corynebacteria
  *Corynebacterium diphtheria*
Pneumococci
  *Diplococcus pneumoniae*
Streptococci
  *Streptococcus pyrogens*
  *Streptococcus salivarus*
Staphylococci
  *Staphylococcus aureus*
  *Staphylococcus albus*
*Neisseria*
  *Neisseria meningitidis*
  *Neisseria gonorrhea*
Enterobacteriaciae
Coliform
  *Escherichia coli*
  *Aerobacter aerogenes*
  *Klebsiella pneumoniae*
Salmonellae
  *Salmonella typhosa*
  *Salmonella choleraesuis*
  *Salmonella typhimurium*
Shigellae
  *Shigella dysenteria*
  *Shigella schmitzii*
  *Shigella arabinotard*
  *Shigella flexneri*
  *Shigella boydii*
  *Shigella sonnei*
Other enteric bacilli
  *Proteus vulgaris*
  *Proteus mirabilis*
  *Proteus* species
  *Proteus morgani*
  *Pseudomonas aeruginosa*
  *Alcaligenes faecalis*
  *Vibrio cholerae*
*Hemophilus-Bordetella* Group
  *Hemophilus influenza,*
  *Hemophilus ducryi*
  *Hemophilus hemophilus*
  *Hemophilus aegypticus*
  *Hemophilus parainfluenza*
  *Bordetalla pertussis*
Pasteurellae
  *Pasteurella pestis*
  *Pasteurella tulareusis*
Brucellae
  *Brucella melitensis*
  *Brucella abortus*
  *Brucella suis*
Aerobic Spore-forming Bacilli
  *Bacillus anthracis*
  *Bacillus subtilis*
  *Bacillus megaterium*
  *Bacillus cereus*
Anaerobic Spore-Forming Bacilli
  *Clostridium botulinum*
  *Clostridium tetani*
  *Clostridium perfringens*
  *Clostridium novyi*
  *Clostridium septicum*
  *Clostridium histolyticum*
  *Clostridium tertium*
  *Clostridium bifermentans*
  *Clostridium sporogenes*
Mycobacteria
  *Mycobacterium tuberculosis hominis*
  *Mycobacterium bovis*
  *Mycobacterium avium*
  *Mycobacterium leprae*
  *Mycobacterium paratuberculosis*
Actinomycetes (fungus-like Bacteria)
  *Actinomyces Isaeli*
  *Actinomyces bovis*
  *Actinomyces naeslundii*
  *Nocardia asteroides*
  *Nocardia brasiliensis*
The Spirochetes
  *Treponema pallidum*
  *Treponema pertenue*
  *Treponema carateum*
  *Borrelia recurrentis*
  *Leptospira icterohemorrhagiae*
  *Leptospira canicola*
  *Trypanasomes*
Mycoplasmas
  *Mycoplasma pneumoniae*
Other Pathogens
Rickettsiae (bacteria-like parasites)
  *Rickettsia prowazekii*
  *Rickettsia mooseri*
  *Rickettsia rickettsii*
  *Rickettsia conori*
  *Rickettsia australis*
  *Rickettsia sibiricus*
  *Rickettsia akari*
  *Rickettsia tsutsugamushi*
Chlamydia (unclassifiable parasitesbacterial/viral)
Chlamydia agents (naming uncertain)
Fungi
  *Cryptococcus neoformans*
  *Blastomyces dermatidis*
  *Hisoplasma capsulatum*
  *Coccidioides immitis*
  *Paracoccidioides brasiliensis*
  *Candida albicans*
  *Aspergillus fumigatus*
  *Mucor corymbifer* (*Absidia corymbifera*)
  *Rhizopus oryzae*
  *Rhizopus arrhizua*
  *Phycomycetes*
  *Rhizopus nigricans*
  *Sporotrichum schenkii*

*Flonsecaea pedrosoi*
*Fonsecacea compact*
*Fonsecacea dermatidis*
*Cladosporium carrionii*
*Phialophora verrucose*
*Aspergillus nidulans*
*Madurella mycetomi*
*Madurella grisea*
*Allescheria boydii*
*Phialophora jeanselmei*
*Microsporum gypseum*
*Trichophyton mentagrophytes*
*Keratinomyces ajelloi*
*Microsporum canis*
*Microsporum adouini*
*Trichophyton rubrum*
Viruses
  Adenoviruses
  Herpes Viruses
    Herpes simplex
    Varicella (Chicken pox)
    Herpes Zoster (Shingles)
    Virus B
    Cytomegalovirus
  Pox Viruses
    Variola (smallpox)
    Vaccinia
    Poxvirus bovis
    Paravaccinia
    Molluscum contagiosum
  Picornaviruses
    Poliovirus
    Coxsackievirus
    Echoviruses
    Rhinoviruses
  Myxoviruses
    Parainfluenza (1-4)
    Mumps Virus
    Newcastle Disease Virus
    Measles Virus
    Rinderpest Virus
    Canine Distemper Virus
    Respiratory Syncytial Virus
    Rubella Virus
  Arboviruses
    Eastern Equine Encephalitis Virus
    Western Equine Encephalitis Virus
    Sindbis Virus
    Chikugunya Virus
    Semliki Forest Virus
    Mayora Virus
    St. Louis Encephalitis Virus
    *Rickettsia prowazekii*
    California Encephalitis Virus
    Colorado Tick Fever Virus
    Yellow Fever Virus
    Dengue Virus
  Reoviruses
    Reovirus Types 1-3
  Retroviruses
    Human Immunodeficiency Viruses I and II (HIV)
    Human T-cell Lymphotrophic Virus I & II (HTLV)
  Hepatitis
    Hepatitis A Virus
    Hepatitis B Virus
    Hepatitis C Virus
  Tumor Viruses
    Rauscher Leukemia Virus
    Gross Virus
    Maloney Leukemia Virus
    Human Papilloma Virus In addition, it may be desirable to detect normal or diseased tissue or cells of a patient. The presence or absence of certain circulating cancer or other cells, for example, may be diagnostic for disease. Thus, the endogenous cells of a human patient are analytes that may be advantageously detected using the compositions, methods and kits of the present invention.

The term "affinity molecule" as used herein refers to any molecule that is capable of specifically binding another molecule. In one embodiment, the affinity molecule is an antibody. In another embodiment, the affinity molecule is an antigen. In other embodiments of the invention, affinity molecules can include, without limitation: nucleic acids (DNA, RNA, PNA and nucleic acids that are mixtures thereof or that include nucleotide derivatives or analogs); biological receptor molecules, such as the insulin receptor; ligands for receptors (e.g., insulin for the insulin receptor); and biological, chemical or other molecules that have affinity for another molecule, such as biotin and avidin. The affinity molecules of the present invention need not comprise an entire naturally occurring molecule but may consist of only a portion, fragment or subunit of a naturally or non-naturally occurring molecule, as for example the Fab fragment of an antibody. The affinity molecule may further comprise a marker that can be detected.

Affinity molecules may be generated by any method known in the art. For example, antibodies may be found in an antiserum, prepared from a hybridoma tissue culture supernatant or ascites fluid, or may be derived from a recombinant expression system, as will be well known in the art. Fragments, portions or subunits of e.g., an antibody, receptor or other species, may be generated by chemical, enzymatic or other means, yielding for example, well-known (e.g., Fab, Fab') or novel molecules. The present invention also contemplates that affinity molecules can include recombinant, chimeric and hybrid molecules, such as humanized and primatized antibodies, and other non-naturally occurring antibody forms. Those skilled in the art will recognized that the non-limiting examples given above describing various forms of antibodies can also be extended to other affinity molecules such that recombinant, chimeric, hybrid, truncated etc., forms of non-antibody molecules can be used in the methods of the present invention.

By the terms "specifically binding" and "specific binding" as used herein is meant that an antibody or other molecule, especially an affinity molecule of the invention, binds to a target such as an antigen, ligand or other analyte, with greater affinity than it binds to other molecules under the specified conditions of the present invention. Antibodies or antibody fragments, as known in the art, are polypeptide molecules that contain regions that can bind other molecules, such as antigens. In various embodiments of the invention, "specifically binding" may mean that an antibody or other affinity molecule, binds to a target analyte molecule with at least about a $10^6$-fold greater affinity, preferably at least about a $10^7$-fold greater affinity, more preferably at least about a $10^8$-fold greater affinity, and most preferably at least about a $10^9$-fold greater affinity than it binds molecules unrelated to the target molecule. Typically, specific binding refers to affinities in the range of about $10^6$-fold to about $10^9$-fold greater than non-specific binding. In some embodiments, specific binding may be characterized by affinities greater than $10^9$-fold over non-specific binding. Whenever a range appears herein, as in "1-10 or one to ten, the range refers without limitation to each integer or unit of measure in the given range. Thus, by 1-10 it is meant each of 1, 2, 3, 4, 5, 6, 7, 8, 9, 10 and any subunit in between.

"Polyclonal Antibodies" or "PAbs," are heterogeneous populations of antibody molecules derived from the sera of animals immunized with an antigen, or an antigenic functional derivative thereof. For the production of polyclonal antibodies, host animals such as rabbits, mice and goats, may be immunized by injection with an antigen or hapten-carrier conjugate, optionally supplemented with adjuvants. Polyclonal antibodies may be unpurified, purified or partially purified from other species in an antiserum. Techniques for the preparation and purification of polyclonal antibodies are well-known in the art and are described in various general and more specific references, including but not limited to Kabat & Mayer, Experimental Immunochemistry, 2d ed., (Thomas, Springfield, Ill. (1961)); Harlow & Lane, Antibodies: A Laboratory Manual (Cold Spring Harbor Laboratory Press, Cold Spring Harbor, N.Y. (1988)); and Weir, Handbook of Experimental Immunology, 5th ed. (Blackwell Science, Cambridge, Mass. (1996)).

"Monoclonal antibodies," or "blabs", which are homogeneous populations of antibodies to a particular antigen, may be obtained by any technique that provides for the production of antibody molecules, such as by continuous culture of cell lines. These techniques include, but are not limited to the hybridoma technique of Köhler and Milstein, *Nature*, 256: 495-7 (1975); and U.S. Pat. No. 4,376,110), the human B-cell hybridoma technique (Kosbor, et al., *Immunology Today*, 4:72 (1983); Cote, et al., *Proc. Natl. Acad. Sci. USA*, 80:2026-30 (1983)), and the EBV-hybridoma technique (Cole, et al., in Monoclonal Antibodies And Cancer Therapy, Alan R. Liss, Inc., New York, pp. 77-96 (1985)). Such antibodies may be of any immunoglobulin class including IgG, IgM, IgE, IgA, IgD and any subclass thereof. The hybridoma producing the MAb of this invention may be cultivated in vitro or in vivo. Production of high titers of MAbs in vivo makes this a presently preferred method of production.

In addition, techniques developed for the production of "chimeric antibodies" (Morrison, et al., *Proc. Natl. Acad. Sci.*, 81:6851-6855 (1984); Takeda, et al, *Nature*, 314:452-54 (1985)) by splicing the genes from a mouse antibody molecule of appropriate antigen specificity together with genes from a human antibody molecule of appropriate biological activity can be used. A chimeric antibody can be a molecule in which different portions are derived from different animal species, such as those having a variable region derived from a murine MAb and a human immunoglobulin constant region.

Alternatively, techniques described for the production of single chain antibodies (U.S. Pat. No. 4,946,778; Bird, *Science* 242:423-26 (1988); Huston, et al, *Proc. Natl. Acad. Sci. USA*, 85:5879-83 (1988); and Ward, et al., *Nature*, 334:544-46 (1989)) can be adapted to produce gene-single chain antibodies suitable for use in the present invention. Single chain antibodies are typically formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments that can be produced by pepsin digestion of the antibody molecule and the Fab fragments that can be generated by reducing the disulfide bridges of the F(ab')$_2$ fragments. Alternatively, Fab expression libraries may be constructed (Huse, et al., *Science*, 246:1275-81 (1989)) to allow rapid and easy identification of monoclonal Fab fragments with the desired specificity.

The term "hapten" as used herein, refers to a small proteinaceous or non-protein antigenic determinant which is capable of being recognized by an antibody. Typically, haptens do not elicit antibody formation in an animal unless part of a larger species. For example, small peptide haptens are frequently coupled to a carrier protein such as keyhole limpet hemocyanin in order to generate an anti-hapten antibody response. "Antigens" are macromolecules capable of generating an antibody response in an animal and being recognized by the resulting antibody. Both antigens and haptens comprise at least one antigenic determinant or "epitope," which is the region of the antigen or hapten which binds to the antibody. Typically, the epitope on a hapten is the entire molecule.

"Receptor" or "biological receptor" typically refers to a molecular structure within or on the surface a cell characterized by selective binding of a specific substance (e.g. a "ligand") and resulting in a specific physiologic effect that accompanies the binding. Examples of receptors include cell surface receptors for peptide hormones, neurotransmitters, antigens, complement fragments and immunoglobulins and cytoplasmic receptors for steroid hormones. As used herein, however, the receptor will typically be isolated and purified and need not effect or be capable of effecting a physiological or other biological effect. The methods of the present invention exploit the selective binding of the receptor to the specific substance.

The term "ligand" refers generally to a molecule that binds to a receptor. Typically, a ligand is a small, soluble molecule, such as a hormone or neurotransmitter.

The term "solid support" refers any solid phase that can be used to immobilize e.g., an analyte, an antibody or a complex. Suitable solid supports will be well known in the art and include the walls of wells of a reaction tray, such as a microtiter plate, the walls of test tubes, polystyrene beads, paramagnetic or non-magnetic beads, nitrocellulose membranes, nylon membranes, microparticles such as latex particles, and sheep (or other animal) red blood cells. Typical materials for solid supports include, but are not limited to, polyvinyl chloride (PVC), polystyrene, cellulose, nylon, latex and derivatives thereof. Further, the solid support may be coated, derivatized or otherwise modified to promote adhesion of the desired molecules (e.g., analytes) and/or to deter non-specific binding or other undesired interactions. The choice of a specific "solid phase" is usually not critical and can be selected by one skilled in the art depending on the assay employed. Thus, latex particles, microparticles, paramagnetic or non-magnetic beads, membranes, plastic tubes, walls of microtiter wells, glass or silicon chips, and red blood cells are all suitable sold supports. Conveniently, the solid support can be selected to accommodate various detection methods. For example, 96 or 384 well plates can be used for assays that will be automated, for example by robotic workstations, and/or those that will be detected using, for example, a plate reader. For methods of the present invention that may involve an autoradiographic or chemiluminescent detection step utilizing a film-based visualization, the solid support may be a thin membrane, such as a nitrocellulose or nylon membrane. According to one embodiment of the invention in which sandwich immunoassays are performed, the walls of the wells of a reaction tray are typically employed. In alternative embodiments of the instant invention, paramagnetic beads may be used as a solid support. Suitable methods for immobilizing molecules on solid phases include ionic, hydrophobic, covalent interactions and the like, and combinations thereof. However, the method of immobilization is not typically important, and may involve uncharacterized adsorption mechanisms. A "solid support" as used herein, may thus refer to any material which is insoluble, or can be made insoluble by a subsequent reaction. The solid support can be chosen for its intrinsic ability to attract and immobilize a capture reagent. Alternatively, the solid phase can retain an additional receptor which has the ability to attract and immobilize a capture reagent. The additional receptor may include a substance that is oppositely charged with respect to either the capture reagent itself or to a charged substance conjugated to the capture reagent. In yet another embodiment of the invention, an additional receptor molecule can be any specific binding member which is immobilized upon (attached to) the solid phase and which has the ability to immobilize a capture reagent through a specific binding reaction. The additional receptor molecule enables indirect immobilization of the capture reagent to a solid phase before or during the performance of the assay. The solid phase thus can be a plastic, derivatized plastic, paramagnetic or non-magnetic metal, glass or silicon surface of a test tube, microtiter well, sheet, bead, microparticle, chip, or other configurations known to those of ordinary skill in the art.

"Peptide" generally refers to a short chain of amino acids linked by peptide bonds. Typically peptides comprise amino acid chains of about 2-100, more typically about 4-50, and most commonly about 6-20 amino acids. "Polypeptide" generally refers to individual straight or branched chain sequences of amino acids that are typically longer than peptides. "Polypeptides" usually comprise at least about 100 to 1000 amino acids in length, more typically at least about 150 to 600 amino acids, and frequently at least about 200 to about 500 amino acids. "Proteins" include single polypeptides as well as complexes of multiple polypeptide chains, which may be the same or different. Multiple chains in a protein may be characterized by secondary, tertiary and quaternary structure as well as the primary amino acid sequence structure; may be held together, for example, by disulfide bonds; and may include post-synthetic modifications such as, without limitation, glycosylation, phosphorylation, truncations or other processing. Antibodies such as IgG proteins, for example, are typically comprised of four polypeptide chains (i.e., two heavy and two light chains) that are held together by disulfide bonds. Furthermore, proteins may include additional components such as associated metals (e.g., iron, copper and sulfur), or other moieties. The definitions of peptides, polypeptides and proteins include, without limitation, biologically active and inactive forms; denatured and native forms; as well as variant, modified, truncated, hybrid, and chimeric forms thereof. The peptides, polypeptides and proteins of the present invention may be derived from any source or by any method, including, but not limited to extraction from naturally occurring tissues or other materials; recombinant production in host organisms such as bacteria, fungi, plant, insect or animal cells; and chemical synthesis using methods that will be well known to the skilled artisan.

The term "conjugate" as used herein refers to two molecules that have been covalently attached, or otherwise linked together. In one embodiment, a nucleic acid conjugate is generated by covalently linking a nucleic acid to a protein, polypeptide or other affinity molecule. In a preferred embodiment of the invention, the protein, polypeptide or other affinity molecule is covalently attached to a nucleic acid via a linking group to form a conjugate.

A "kit" for detecting the presence of an analyte in a sample by the methods of the invention may, by way of example, comprise at least one container means having disposed therein a binding pair specific for the selected analyte. The kit may further comprise other containers comprising one or more of the following: buffers, solutions or other reagents and materials necessary for performing analyte detection; reagents capable of amplifying the nucleic acid probe components of the binding pairs; and reagents capable of detecting the presence of nucleic acid components following amplification. Preferably, the kit further comprises instructions for use. The kit, if intended for diagnostic use, may also include notification of a FDA approved use and instructions therefor.

Specifically, a compartmentalized kit includes any kit in which reagents are contained in separate containers. Such containers include small glass containers, plastic containers or strips of plastic or paper. Such containers allow the efficient transfer of reagents from one compartment to another compartment such that the samples and reagents are not cross-contaminated and the agents or solutions of each container can be added in a quantitative fashion from one compartment to another. Such containers may include a container which will accept a test sample, a container which contains the probe or primers used in the assay, containers which contain buffers and reagents (such as phosphate buffered saline, Tris-buffers, and the like), and containers which contain the reagents used to detect the marker nucleic acid, amplified product, or the like. One skilled in the art will readily recognize that preformed binding pairs and/or materials, supplies and reagents necessary to prepare binding pairs can readily be incorporated into one of the established kit formats that are well known in the art.

A kit for coupling DNA to an antibody or other affinity molecule by the methods of the invention may comprise at least one container means having disposed therein the lyophilized activated DNA. The kit may further comprise other containers comprising one or more of the following: reagents, buffers and agents capable of detecting the presence of nucleic acid after the reaction. Preferably, the kit further comprises instructions for use. A kit for making or using the novel compositions and methods for isolating and assaying analytes described herein may include the already manufactured microbubble or the thin film used to create the microbubble. Likewise, the microbubble of the kit may or may not already have the attached affinity molecule. The kit may further comprise other containers comprising one or more of the following: reagents, buffers and agents capable of making the microbubbles or useful in employing them for methods of affinity isolation, purification, concentration, etc. Preferably, the kit further comprises instructions for use. One skilled in the art will readily recognize that compositions and methods described in the present invention can readily be incorporated into one of the established kit formats that are well known in the art.

The present invention provides novel compositions and methods for isolating and assaying analytes, including also cells, viruses, cellular subcomponents and soluble molecules from solution. It relies on coated microbubbles to specifically bind the target analyte (cell, virus, cellular subcomponent or soluble molecule). According to the invention, microbubbles are coated with, or otherwise made to exhibit on their exterior surface, an affinity molecule. The novel compositions and methods of the present invention can also be used to concentrate analytes, including but not limited to antibodies, antigens, proteins and nucleic acids.

In one embodiment, the affinity-molecule coated microbubbles further comprise a detectable marker. In still another embodiment, the affinity molecule itself is the detectable marker. In these embodiments, the amount, or present or absence of the analyte, species, or microbubble may be quantified or detected by virtue of the marker. In one embodiment, the marker on the microbubble is a nucleic acid that may be amplified and detected. The techniques used to accomplish detection may include, but are not limited to, PCR, nucleotide sequencing, PCR sequencing, molecular beacon technology, hybridization, hybridization followed by PCR, fluorescence, radiolabelling, phosphorescence and absorbance. Examples of reagents that may be used for detection include, but are not limited to, radiolabels, enzymatic labels (e.g. horseradish peroxidase, alkaline phosphatase), fluorescence, phosphorescence, bioluminescence, chemiluminescence, affinity labels (e.g. biotin, avidin, or streptavidin) and other reagents well known by those of skill in the art. These embodiments are not limiting, and other embodiments can be envisioned being used with the invention.

In one embodiment of the invention, the microbubbles are protein microbubbles, which can be comprised of any peptide, polypeptide, protein or combinations thereof. Both synthetic and naturally occurring peptides, polypeptides, proteins and combinations are contemplated by the invention. In one embodiment, the protein microbubbles can be readily formed into microbubbles through the introduction of a gas. In one embodiment, the protein is albumin.

The protein microbubbles of the invention are typically formed by the introduction of a gas into a solution of protein, for example, by sonication. The bubbles can be filled with any gas, including, but not limited to oxygen, nitrogen, carbon dioxide, helium, fluorocarbon gases and various combinations thereof, such as air. In one aspect of the invention, gas may be introduced into the protein through a process comprising heating a solution of protein. Without being limited to a specific theory, heating may serve to stabilize the protein microbubbles by denaturing the protein. In another embodiment, the protein microbubbles may be stabilized, for example, by denaturing the protein, fixing the protein, crosslinking the protein or treatment with $Cr^{+++}$. In one aspect, the microbubbles are stabilized by cross linking with aldehydes such as glutaraldehyde or formaldehyde.

Protein microbubbles are generally in the range of 0.1 to 100 microns, typically 1 to 50, and frequently 2 to 20 or 2 to 30 microns in diameter.

According to the invention, the affinity molecule can be a receptor, a ligand, or an antibody. Alternatively, the affinity molecule can be biotin, avidin or streptavidin. In one embodiment of the invention, the microbubbles are biotinylated and then coated with streptavidin, which creates a microbubble that can be readily coated with a biotinylated ligand such as an antibody. In another embodiment, the microbubbles bubbles are ligand-coated microbubbles.

Coating of microbubbles with an affinity molecule can be accomplished by any method known in the art. Advantageously, proteins contain amine functional groups that can serve as the basis for numerous modifications and coupling reaction, such as reaction with aldehydes. Furthermore, the skilled artisan will recognize that the materials that make up microbubbles, e.g. protein, glass and the like, can be chemically derivatized or functionalized to covalently interact with various types of affinity molecules. The skilled artisan will be familiar with a variety of commercial reagents, products and kits for coupling proteins and other molecules to the microbubbles of the invention. The affinity molecule may be directly coupled to the protein, for example, by using a heterobifunctional reagent such as sulfosuccinimidyl 4-(N-maleimidomethyl)cyclohexane-1-carboxylate.

In another embodiment of the invention, the affinity molecule is indirectly coupled to the protein, such as through the interaction of at least one other molecule. In one aspect of the invention, microbubbles are directly coupled to streptavidin and the affinity molecule is biotinylated, such that the streptavidin and biotin interact to couple the affinity molecule to the protein. The interactions of biotin and avidin/streptavidin are well known in the art, as are methods for coupling these molecules to other species. Reference may also be made to a general or more specific textbook or laboratory manual describing the chemistry, biology, and interactions of biotin, avidin and streptavidin, and/or the methods for coupling biotin and avidin/streptavidin to other molecules. See e.g., *Avidin-Biotin Chemistry: A Handbook* (Savage, et. al., eds. Pierce Chemical Co., Rockford, Ill., 1992)

In another aspect of the invention, coated microbubbles are made using glass microbubbles such as those supplied by 3M™. Borosilicate glass bubbles can be treated with sodium hydroxide to expose a silica surface and then reacted with a silanating agent such as an 3-amino-propyl-triethoxy silane, creating a surface coated with a primary amines. The microbubble can be reacted with NHS-biotin to form a biotinylated glass microbubble, which can then be coated with streptavidin, if desired. This streptavidin microbubble can then be easily coated with a biotinylated ligand such as a biotinylated antibody; alternatively epoxy coated glass micro bubbles can be reacted directly with ligands or coated directly or indirectly by methods known to those skilled in the art.

In another embodiment of the invention, methods for affinity isolation or affinity assay of a species are provided. According to these embodiments, the method comprises the steps of providing microbubbles coated with an affinity molecule in a solution, contacting the microbubbles with a species that interacts with the affinity molecule in a solution, thereby generating microbubbles coated with the species, and separating the microbubbles coated with the species from the solution—in a preferred embodiment, allowing the microbubbles coated with the species to float to the top of the solution—thereby separating the species from the solution. In this manner, all manner of species may be affinity isolated or affinity assayed including proteins (antigen, antibodies, ligands, receptors, hormones), nucleic acids, lipoproteins, fats, triglycerides, sugars, carbohydrates, viruses, cells, cellular components, subcellular organelles, and components of subcellular organelles, as well as complexes thereof In yet another embodiment of the invention, methods for affinity concentration of a species are provided. According to these embodiments, the method comprises the steps of providing microbubbles coated with an affinity molecule in a solution, contacting the microbubbles with a species that interacts with the affinity molecule in a solution, thereby generating microbubbles coated with the species, and separating the microbubbles coated with the species from the solution—in a preferred embodiment, allowing the microbubbles coated with the species to float to the top of the solution—thereby separating the species from the solution. In this manner, all manner of species may be concentrated such as proteins (antigen, antibodies, ligands, receptors, hormones), nucleic acids, lipoproteins, fats, triglycerides, sugars, carbohydrates, viruses, cells, cellular components, subcellular organelles, and components of subcellular organelles, as well as complexes thereof.

The species that can be isolated, assayed, purified or concentrated can be any manner of material including proteins (antigen, antibodies, ligands, receptors, hormones), nucleic acids (RNA, DNA nucleotide analogs, mixtures thereof, etc), lipoproteins, fats, triglycerides, sugars, carbohydrates, viruses, cells, cellular components (liposomes, endoplasmic reticulum, etc.), subcellular organelles (mitochondria, etc.), and components of subcellular organelles, as well as complexes thereof. In one aspect of this embodiment, the species is a receptor, a ligand, or an antigen. In one embodiment, the species is an analyte. In alternative embodiments, the species is a virus or a cell.

The coated microbubbles of the invention bind to the target species, including cells, viruses, analytes or other molecules and then rise to the surface of the solution, thus separating themselves from the contacting solution and non-target species. In certain embodiments, where the separation time is important, the solution containing the microbubbles may be centrifuged or subjected to a bubble trap to further effect the separation more rapidly.

The albumin microbubbles of the invention have the useful property of being able to be easily destroyed and made to visually disappear by applying pressure or vacuum to the solution, or by adding a small amount of a detergent or surfactant. This aspect of the invention is particularly useful where it is desirable to isolate the target species devoid of the capturing microbubble. For example, it may be desirable to characterize the phenotype of an affinity-isolated cell or to free the isolated cell for further analysis or propagation. The methods of the present invention provide, in some embodiments, a simple means for releasing the species from the capturing microbubble that avoids potentially damaging reagents, such as enzymes, harsh chemicals and extremes of pH. In other embodiments, the analyte or species may be released from the microbubble by enzymatic or chemical means.

Glass microbubbles advantageously can be constructed from borosilicate glass which is largely free of contaminating material. This material is also resistant to breakage or destruction during normal handling.

The microbubbles of the present invention have an additional advantage over solid particles for affinity applications in that in the normal force of gravity and the buoyant force of the microbubble are in different directions, thus resulting in a significant reduction in non specific binding and entrapment of species that typically sink toward the bottom of the reaction vessel during separation. The separation can be enhanced with the unbound cells being forced away from the microbubbles in a low centrifugal field, as with a modest centrifugal speed, under conditions that do not adversely affect the microbubbles.

As described further below under EXAMPLES, experiments with albumin microbubbles coated with an anti-bacteria antibody mixed with a suspension of bacteria have resulted in sterilization of the suspension, with all the bacteria co-isolated with the microbubbles. Similarly, in control experiments the microbubbles without specific antibody showed little non-specific binding, resulting in no detectable bacteria co-purifying with the microbubbles following separation.

The present invention also provides methods for generating microbubbles for use in affinity isolation or affinity assay comprising providing microbubbles; and coating the microbubbles with an affinity molecule.

It will be understood that the application of the teachings of the present invention to a specific problem or situation will be within the capabilities of one having ordinary skill in the art in light of the teachings contained herein. The invention will be further illustrated by reference to the following non-limiting Examples. The following examples, including experiments and results achieved, are provided for illustrative purposes only and are not to be construed as limiting the present invention.

EXAMPLES

Albumin Microbubbles

Example 1

Preparation of Albumin Microbubbles

Albumin solution (Human) 5%, USP (Bayer Corporation, Elkhart, Ind.) was diluted to 1% with air-saturated normal saline at room temperature. Twenty milliliters of the diluted solution was placed into a 50 ml glass beaker and immersed in a 85° C. water bath below the 25 ml level on the beaker. The temperature of the albumin solution was monitored using digital thermometer with gentle stirring of the solution. At a process temperature of 73° C., the probe of a Branson Digital Sonifier®, Model 450 (Branson Ultrasonics Corp., Danbury, Conn.) was placed in contact with the surface of the albumin solution and immediately sonicated at 80% amplitude for 10 seconds. The beaker was removed from the water bath, placed in crushed ice, and stirred gently until the temperature was reduced to 40° C. The albumin microbubble suspension was transferred to a 150 ml flexible carboy (Flexboy® Bag, Stedim, Concord, Calif.) at room temperature. The process was repeated several times with fresh solution until the bag was filled. The microbubble suspension was adjusted to 0.05% sodium azide and the bag stored vertically under refrigeration for at least 24 hours. The sonication process converted approximately 5% of the soluble albumin to insoluble, air-filled albumin microbubbles.

Example 2

Preparation of Chromium-Stabilized Albumin Microbubbles

In some experiments, albumin microbubbles were stabilized by treatment with $Cr^{+++}$. Albumin microbubbles were allowed to float and the liquid phase was removed and replaced with 5 mM chromium potassium sulfate. The microbubbles were maintained in suspension by gentle agitation and incubated in a water bath at 60° C. for 30 minutes. Following incubation, the chromium solution was removed by washing as described below, and replaced with 1% human serum albumin in normal saline. Chromium treated albumin microbubbles were treated as described for untreated microbubbles.

Example 3

Preparation of Biotin-Coated Albumin Microbubbles

Unconverted albumin solution was drained away from underneath the floating layer of microbubbles and replaced by cold, air-saturated phosphate buffered saline, pH 7.4 (PBS), containing 0.2% polyvinyl alcohol (MW 30,000-70,000) (PVA/PBS). The microbubbles were resuspended by gentle agitation and transferred to disposable plastic syringes equipped with a bottom-mounted stopcock. The microbubbles were washed free of residual soluble albumin by repeated centrifugation at 200×g, at 4° C. for 5 min, draining, and replenisment of the solution with fresh cold, air-saturated PVA/PBS. The washed albumin microbubbles were suspended at approximately 25% v/v in PVA/PBS and biotinylated by reaction with sulfosuccinimidyl-6-(biotinamido) hexanoate (sulfo-NHS-LC-biotin; BZ-Link™ sulfo-NHS-LC-biotin, Pierce Biotechnology, Inc., Rockford, Ill.) at a concentration of 0.01 to 1.0 mg/ml under gentle agitation at room temperature for at least one hour. Unreacted biotin was removed by several centrifugal washings with cold, air-saturated PVA/PBS at 4° C. The extent of biotin labeling was assessed by dissolving an aliquot of suspended microbubbles in PVA/PBS containing 0.1% Triton X-100 and determining the concentrations of protein (BCA Protein Assay, Pierce) and biotin (2-(4'-hydroxyazobenzene)-benzoic acid assay). Typical biotinylation reactions of albumin microbubbles yield molar ratios of 40% to 500% biotin to albumin. The availability of biotin on the surface of the albumin microbubbles was confirmed by observing the spontaneous association of biotin-microbubbles with BioMag Nuclease Free Streptavidin paramagnetic particles (Polysciences, Inc., Warrington, Pa.) in suspension. The biotin-coated albumin microbubbles were stored under refrigeration in PVA/PBS containing 0.05% sodium azide.

Example 4

Preparation of Streptavidin-Coated Albumin Microbubbles

Air-filled albumin microbubbles were coated with streptavidin (Prozyme, San Leandro, Calif.) indirectly by exposing biotin-microbubbles to an excess of streptavidin. Under these conditions, cross-linking of microbubbles is avoided. Streptavidin was also coated onto albumin microbubbles directly via a bifunctional protein cross-linking reagent.

For indirect coating, a suspension of biotin-coated albumin microbubbles suspended in PVA/PBS was treated completely and rapidly by addition of 10 mg/ml solution of streptavidin to yield a final concentration of 1 mg/ml, with continuous vortex mixing. Unreacted streptavidin was removed by repeated centrifugal washing as described above. The tetravalent nature of streptavidin ensured that biotin binding sites were still available.

Alternatively, albumin microbubbles were coated directly with streptavidin using sulfosuceinimidyl 4-(N-maleimidomethyl)cyclohexane-1-carboxylate (s-SMCC). Streptavidin at 10 mg/ml in PBS, pH 7.4, was treated with a 5 to 10-fold molar excess of n-succinimidyl S-acetylthioacetate (SATA) for at least 1 hour at room temperature. Unreacted SATA was removed from the streptavidin by FPLC using a Sephadex G-25 resin equilibrated in PBS, and the purified protein was stored frozen. Just prior to use, the protective acetyl group was removed from the modified streptavidin by treatment with PBS containing 50 mM hydroxylamine and 2.5 mM EDTA, pH 7.5, for 2 hours at room temperature. Simultaneously, a suspension of albumin microbubbles suspended in PVA/PBS was treated with 0.01 to 1 mg/ml s-SMCC under gentle agitation for 30 min at room temperature. Excess s-SMCC reagent was immediately removed by centrifugal washing (repeated 4 times), and the s-SMCC microbubbles were combined with the sulfhydryl-modified streptavidin. The streptavidin becomes covalently coupled to the surface of the albumin microbubbles by reaction of the maleimide functional group with the freshly exposed streptavidin sulfhydryl group. The microbubbles were washed free of excess streptavidin by repeated centrifugal washings, suspended in cold, air-saturated PBS containing 0.05% sodium azide and stored under refrigeration.

Example 5

Coating Albumin Microbubbles with Antibody

Affinity-purified antibody to *E. coli* 0157:H7 was obtained from KPL (Gaithersburg, Md.) and biotinylated as described below. The antibody was dissolved in PBS, pH 7.4 and warmed to 37° C. for 30 min. The warmed solution was treated with an 8-12 fold molar excess of sulfosuccinimidyl-6-(biotinamido) hexanoate (EZ-Link™ sulfo-NHS-LC-biotin) for 2 hrs at room temperature. Excess biotin reagent was removed by G-25 Sephadex gel filtration chromatography, eluting with PBS. The biotinylated antibody was concentrated by ultra-filtration using a Microcon® YM-30 Filter Device (Millipore, Bedford, Mass.) and stored under refrigeration in the presence of sodium azide as preservative. Avidin-coated albumin microbubbles were resuspended by gentle agitation and combined with a molar excess of biotin-labeled antibody in PBS. Excess material was removed from the insoluble microbubbles by repeated centrifugation and resuspension as described above. The antibody-coated albumin microbubbles were stored in PVA/PBS containing sodium azide, at 4° C.

Example 6

Capture of Bacterial Cells on Antibody-Coated Microbubbles

*E. coil* 0157:H7 was obtained from American Type Culture Collection (Manassas, Va.) and propagated on Luria Bertani (LB) liquid and agar media at 37° C. Bacteria grown in liquid media were serially diluted in cold, sterile PVA/PBS or PBS containing 0.2% BSA (BSA/PBS) to a density of approximately 5,000 cells/ml. One-tenth volume of microbubble suspension was added to the cell suspension and gently agitated for several minutes at room temperature. The microbubbles were allowed to float to the surface of the mixture by natural buoyancy over 10 minutes. Ten microliters of the underlying liquid phase, cleared of floating microbubbles, was removed by micropipette, streaked onto an LB agar plate and incubated overnight at 37° C. Positive control samples of bacterial suspension yielded approximately 50 colonies/plate. Bacterial suspension treated with antibody-coated microbubbles were depleted of colony forming cells. The bacterial cells could be recovered from the microbubbles by gently agitating the microbubble suspension and plating 10 µl of the suspension, as evidenced by colonies formed on the resulting LB plates after overnight incubation. This result indicates that bacterial cells are captured by antibody-coated albumin microbubbles. Bacterial suspensions treated with either uncoated or streptavidin-coated albumin microbubbles failed to remove cells from suspension.

Example 7

Preparation of Microbubbles By First Modifying Albumin Followed by Sonication

Albumin microbubbles prepared from biotinylated serum albumin by labeling the serum albumin with biotin prior to microbubble formation, were found to bind avidin and/or streptavidin. Bovine Serum Albumin (BSA; Bovuminar Cohn Fraction V, intergen, Purchase, N.Y.) was dissolved in normal saline, containing 4 mM sodium caprylate and 4 mM sodium tryptophanate to 50 mg/ml, sterile filtered and stored in a clear glass container, under fluorescent lighting at room temperature for two weeks. This treatment photo-oxidized free sulfhydryl groups that can interfere with microbubble formation. Twenty milliliters of the BSA solution was removed and adjusted to pH 8.5 with 1 M NaOH. Twenty-five micrograms of s-NHS-LC-biotin was added with mixing and the pH maintained at 8.5 for 1 hour at room temperature. The reaction was diluted to 1% albumin by the addition of normal saline and subjected to the sonication process as described above for unmodified human albumin. The resulting albumin microbubbles were washed several times with 1% BSA in normal saline to remove unincorporated biotin. The microbubbles prepared from biotinylated albumin were reactive with avidin or streptavidin and could be coated with avidin or streptavidin as described above.

Glass Microbubbles

Example 8

Preparation of Amine-Coated Glass Microbubbles

3M™ ScotchLite™ Glass Bubbles S60HS (St Paul, Minn.), having a density of about 0.6 g/cc and an average diameter of about 30 µm, were suspended in water and allowed to float to the top of the suspension. The liquid layer was drained from the bottom to remove fines and shards. This was conveniently performed in a 60 cc disposable syringe fitted with a stopcock mounted on the tip. The washing was repeated several times. Reactive surface hydroxyl residues were provided by suspension of the washed microbubbles in 0.25 M NaOH for 24 hours at 60° C., followed by washing with water to remove the alkali. The microbubbles were subsequently treated with 0.05 M HCl for 1 hour at room temperature. The acid was removed by washing with water, followed by dry acetone, and finally the product was dried in an oven at 60° C. The hydroxyl functions were converted to amino groups by suspending the treated, dried glass microbubbles in a 3% solution of 3-aminopropyltriethoxy silane (3-APS, Sigma) in dry acetone or toluene, for 30 minutes at room temperature. Excess silane was removed by several washings with acetone, and the derivatized microbubbles were oven dried at 60° C.

In some experiments, the glass microbubbles were suspended in 70% sulfuric acid and 9% hydrogen peroxide for 16 hours at room temperature, followed by exhaustive washing with water. The acid-treated microbubbles were resuspended in a solution of 3-APS:water:ethanol (3:4:92 by volume) prepared just prior to use. The reaction was allowed to proceed for 30 minutes at room temperature. Excess reagent was removed by washing in ethanol, and the glass microbubbles baked at 115° C. for 1 hour. The microbubbles were washed again in ethanol and oven dried at 60° C.

Amine-coated glass microbubbles were stored dry at room temperature. The presence of functional surface amine groups at 2.5-3.0/nm$^2$ was confirmed by analysis using s-succinimidyl-4-O-(4,4'dimethoxytrityl)butyrate (Pierce).

Example 9

Coating Amine-Glass Microbubbles with Antibody

Amine-coated glass microbubbles were suspended in 50 mM sodium bicarbonate, 0.1% Tween™ 20, pH 8.5, and reacted with sulfo-NHS-LC-biotin for two hours at room temperature. The biotin reagent was present at a 0.1 to 7-fold excess over available surface amines. The glass microbubbles were washed and stored in PBS containing 0.1% Tween™ 20 (PBS/Tween)™. Avidin, dissolved in water at 5 mg/ml, was added in molar excess to saturate the available biotin sites. Excess avidin was removed by washing with PBS/Tween™ and the microbubbles were stored in PBS, containing 0.2% BSA (BSA/PBS) and 0.05% sodium azide, under refrigeration.

Amine glass microbubbles were also coated with sulfhydryl-modified avidin via s-SMCC cross-linking reagent. Amine glass microbubbles were suspended 1:10 (w/v) in 50 mM sodium phosphate, pH 7.5 containing 10% dimethyl formamide and 2 mg/ml s-SMCC for one hour at room temperature. The maleimide-coated glass bubbles were washed with 100% dry ethanol, drained, dried under vacuum in a glass vial, and stored under nitrogen at −20° C. An excess amount of avidin, modified with SATA to contain free sulfhydryl groups (see Example 4 above), was deacetylated with hydroxylamine and added directly to the dried maleimide glass microbubbles to yield avidin-coated microbubbles. Excess avidin was removed after overnight incubation by washing with PBS/Tween™.

Glass microbubbles (20 mg) coated with avidin were suspended in 1.0 ml PBS/BSA and combined with 10 µg of antibody to *E. coli* 0157:H7, modified to contain 2-6 biotin groups (see Example 5 above). The antibody readily attached to the avidin surface coating within two hours in an ice bath, creating antibody-coated glass microbubbles. These microbubbles were washed and stored at 4° C. as a suspension in an aqueous buffer suitable for maintaining antibody stability. BSA and sodium azide were added as stabilizers.

Example 10

Capture of *E. Coil* 0157 Onto Antibody-Coated Glass Microbubbles

*E. coli* grown in culture was serially diluted in cold, sterile PBS containing BSA and sodium azide to 5,000 cell/ml. The bacterial suspension was treated with 1% (v/w) antibody-coated microbubbles with agitation at room temperature for several minutes. The microbubbles were allowed to float to the surface and 10 µl of underlying liquid layer (cleared by floatation of the microbubbles) was removed and plated onto agar media in parallel with untreated, control samples of bacterial suspension. Bacterial suspensions treated with uncoated microbubbles exhibited no reduction in colonies formed overnight at 37° C. Bacterial suspension treated with antibody-coated glass microbubbles exhibit a 50 to 100% decrease in colony forming units, which were recovered by resuspension and plating. This result confirmed the capture of bacterial cells on glass microbubbles coated with a specific antibody.

Example 11

Coating Epoxy-Glass Microbubbles with Antibody

3M™ ScotchLite™ Glass Bubbles H2O/1000 were washed and suspended in 0.1 M sodium borate, 0.15 M sodium chloride, pH 9.0. Avidin was added at 5 mg/ml and the suspension was incubated at 4° C. for 48 hours. The avidin-coated glass microbubbles were washed in BSA/PBS with 0.05% sodium azide to remove unbound avidin and stored in the same solution. The avidin microbubbles were coated with biotin-labeled antibody to *E. coil* 0157:H7 and used to remove bacterial cells from suspension as described above.

Example 12

Preparation of Cis-Diol Coated Glass Microbubbles

Glass microbubbles with active hydroxyl residues were prepared as described above (see Example 6, above). The dried glass microbubbles were silanized by treatment with dry acetone containing 6% 3-glycidoxypropyltrimethoxysilane (v/v) for 3 hours at room temperature. Excess silane reagent was removed by washing with acetone, followed by suspension in 0.05 M HCl for 2 hours at 60° C. to convert the epoxy function to cis-diol functions. Acid was removed by washing in acetone and the microbubbles were dried overnight at 37° C. The cis-diol glass microbubbles were stored dry at room temperature.

A 25% suspension of cis-diol-coated glass microbubbles was activated with 0.3 M carbonyl diimidizole (CDI) in dry acetone for 1 hour at room temperature in a sealed vessel, with venting every 10 minutes. Excess reagent was removed by washing with dry acetone and the glass microbubbles were dried under vacuum at room temperature. The activated microbubbles were stored dry under nitrogen at 4° C.

CDI-activated glass microbubbles were coated by overnight incubation with 4 mg/ml avidin dissolved in 0.1 M sodium carbonate, pH 9.5 at room temperature. The pH was reduced to 6.5 by the addition of 0.2 M sodium phosphate, monobasic. The avidin-coated glass microbubbles were washed and stored in BSA/PBS containing sodium azide.

Biotin-labeled antibody to *E. coli* O157:H7 was applied and bacteria removed from suspension as previously described above. This experiment gave a 50-100% reduction in bacteria, as evidenced by a reduced number of colonies relative to control samples.

In some experiments, cis-diol-coated glass microbubbles were activated with 0.2 M sodium periodate for 90 minutes at room temperature. The product was washed with water, followed by ethanol and allowed to air-dry at room temperature. This chemistry coated the glass microbubble surface with amine-reactive aldehyde functions. Subsequent coating with avidin, followed by biotinylated antibody and testing, was performed as described above, with similar results.

What is claimed is:

1. A method for generating coated, gas-filled albumin microbubbles for use in affinity isolation or affinity assay comprising:
    (a) heating a solution of albumin;
    (b) sonicating the heated solution from step (a) to introduce gas into the solution wherein the solution does not contain any andehyde or Cr+++, thereby generating albumin microbubbles that have not been stabilized by crosslinking the albumin with an aldehyde or by treatment with Cr+++;
    (c) suspending the albumin microbubbles from step (b) in a buffered solution comprising polyvinyl alcohol; and
    (d) coating the microbubbles from step (c) with an affinity molecule.

2. A method for generating affinity-modified gas-filled protein microbubbles for use in affinity isolation or affinity assay comprising:
    (a) providing a protein in a solution, wherein the protein is coupled to an affinity molecule;
    (b) heating the solution of protein from step (a);
    (c) sonicating the heated solution from step (b) to introduce gas into the solution wherein the solution does not contain any andehyde or Cr+++, thereby generating affinity-modified protein microbubbles, wherein the protein microbubbles are not stabilized by fixing by crosslinking the protein with an aldehyde or by treatment with Cr+++; and
    (d) suspending the affinity-modified protein microbubbles from step (c) in a buffered solution comprising polyvinyl alcohol.

3. A method for generating coated gas-filled microbubbles for use in affinity isolation or affinity assay comprising:
    (a) heating a solution of protein;
    (b) sonicating the heated solution from step (a) to introduce gas into the solution to generate protein microbubbles, wherein the protein microbubbles are not stabilized by crosslinking the protein with an aldehyde or by treatment with Cr+++;
    (c) suspending the protein microbubbles from step (b) in a buffered solution comprising polyvinyl alcohol; and
    (d) coating the microbubbles from step (c) with an affinity molecule.

4. The method of any one of claim 1, 2 or 3, wherein the affinity molecule is selected from the group consisting of a receptor, a ligand, a nucleic acid and an antibody.

5. The method of claim 3, wherein the affinity molecule is biotin.

6. The method of claim 3, wherein the affinity molecule is avidin or streptavidin.

7. The method of any one of claim 1, 2 or 3, wherein the coating comprises covalently coupling the affinity molecule to an amine group on the microbubble.

8. The method of claim 3, wherein the coating comprises covalently coupling the affinity molecule to an epoxy group on the microbubble.

9. The method of any one of claim 1, 2 or 3, wherein the coating comprises coupling the affinity molecule to the microbubble through a heterobifunctional reagent.

10. The method of claim 9 wherein the method further comprises treating microbubbles with the heterobifunctional reagent sulfosuccinimidyl 4-(N-maleimidomethyl)cyclohexane-1-carboxylate (s-SMCC)) to form s-SMCC microbubbles.

11. The method of claim 10 wherein the method further comprises treating the affinity molecule with n-succinimidyl S-acetylthioacetate (SATA), and the protective acetyl group is removed just prior to reaction with s-SMCC microbubbles.

* * * * *